Figure 1:
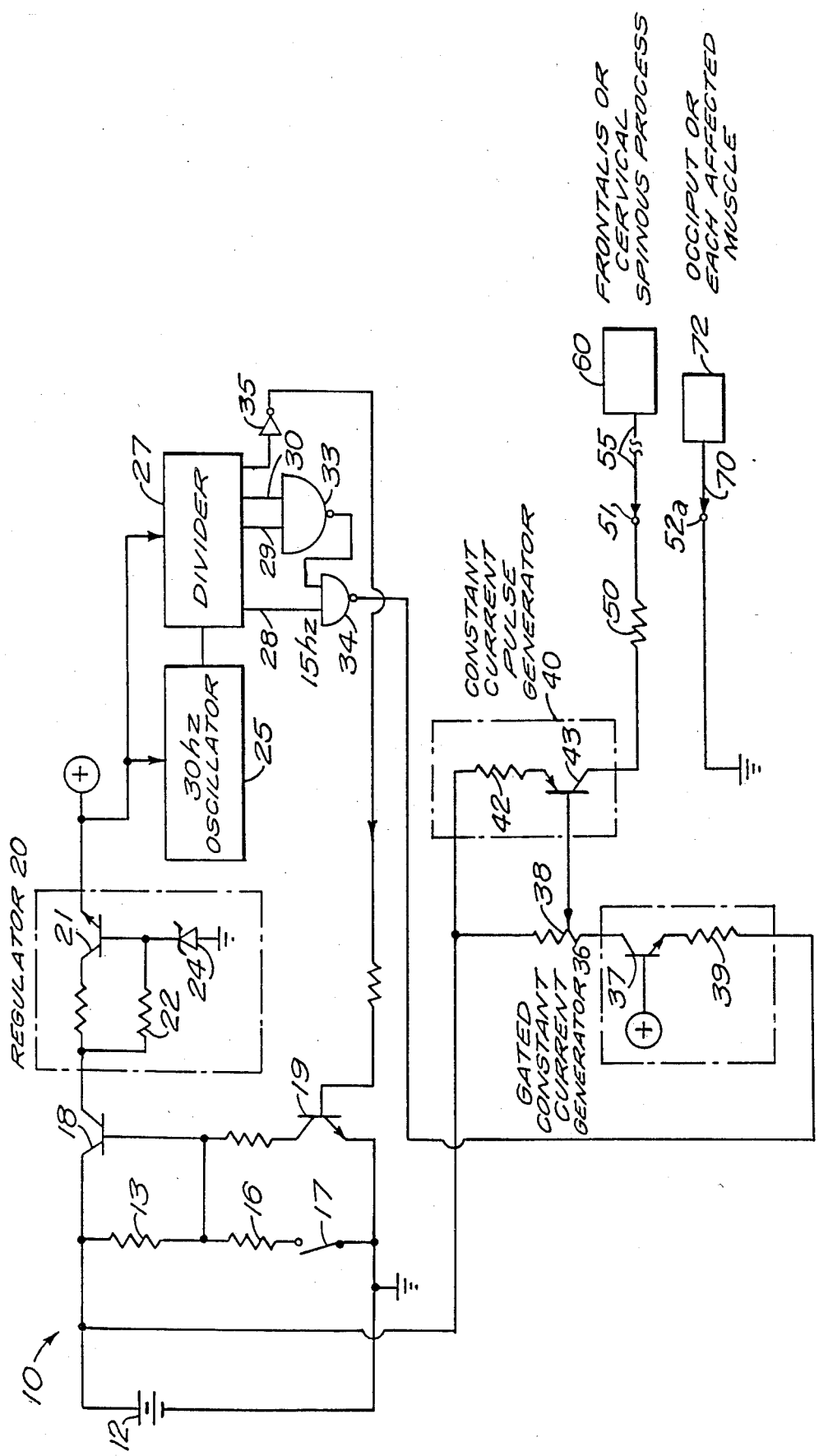

United States Patent [19]

Liss et al.

[11] Patent Number: 4,559,948
[45] Date of Patent: * Dec. 24, 1985

[54] CEREBRAL PALSY TREATMENT APPARATUS AND METHODOLOGY

[75] Inventors: Saul Liss; Bernard Liss, both of Glen Rock, N.J.

[73] Assignee: Pain Suppression Labs, Elmwood Park, N.J.

[*] Notice: The portion of the term of this patent subsequent to Nov. 5, 2002 has been disclaimed.

[21] Appl. No.: 638,502

[22] Filed: Aug. 7, 1984

Related U.S. Application Data

[63] Continuation-in-part of Ser. No. 569,476, Jan. 9, 1984.

[51] Int. Cl.[4] ............................................. A61N 1/00
[52] U.S. Cl. ............................................... 128/419 R
[58] Field of Search ..................... 128/419 R, 421–423

[56] References Cited

U.S. PATENT DOCUMENTS

| | | | |
|---|---|---|---|
| 2,004,751 | 6/1935 | Fischer et al. | 128/423 R |
| 3,640,284 | 2/1972 | DeLangis | 128/422 |
| 3,791,373 | 2/1974 | Winkler et al. | 128/422 |
| 3,902,502 | 9/1975 | Liss et al. | 128/422 |
| 4,109,660 | 8/1978 | Nesmeyanov et al. | 128/419 R |
| 4,155,366 | 5/1922 | DiMucci | 128/421 |
| 4,305,402 | 12/1981 | Katims | 128/421 |
| 4,503,863 | 3/1985 | Katims | 128/421 |

FOREIGN PATENT DOCUMENTS

| | | | |
|---|---|---|---|
| 2500309 | 8/1982 | France | 128/422 |
| 605603 | 5/1978 | U.S.S.R. | 128/421 |

*Primary Examiner*—William E. Kamm
*Assistant Examiner*—Mitchell J. Shein
*Attorney, Agent, or Firm*—Hopgood, Calimafde, Kalil, Blaustein & Judlowe

[57] ABSTRACT

Cerebral palsy treatment apparatus and methodology employs a transcutaneous electronic wave to suppress pain and increase motor function. A first positive contact electrode is placed at the frontalis, and a second negative contact electrode is placed at the occiput of the head. Alternatively, the first positive contact electrode is placed at the cervical spinous process and the second negative contact electrode is placed at each affected muscle. An electronic current wave comprising relatively high frequency pulses with a low frequency amplitude modulation is then applied between the first to the second electrodes.

5 Claims, 5 Drawing Figures

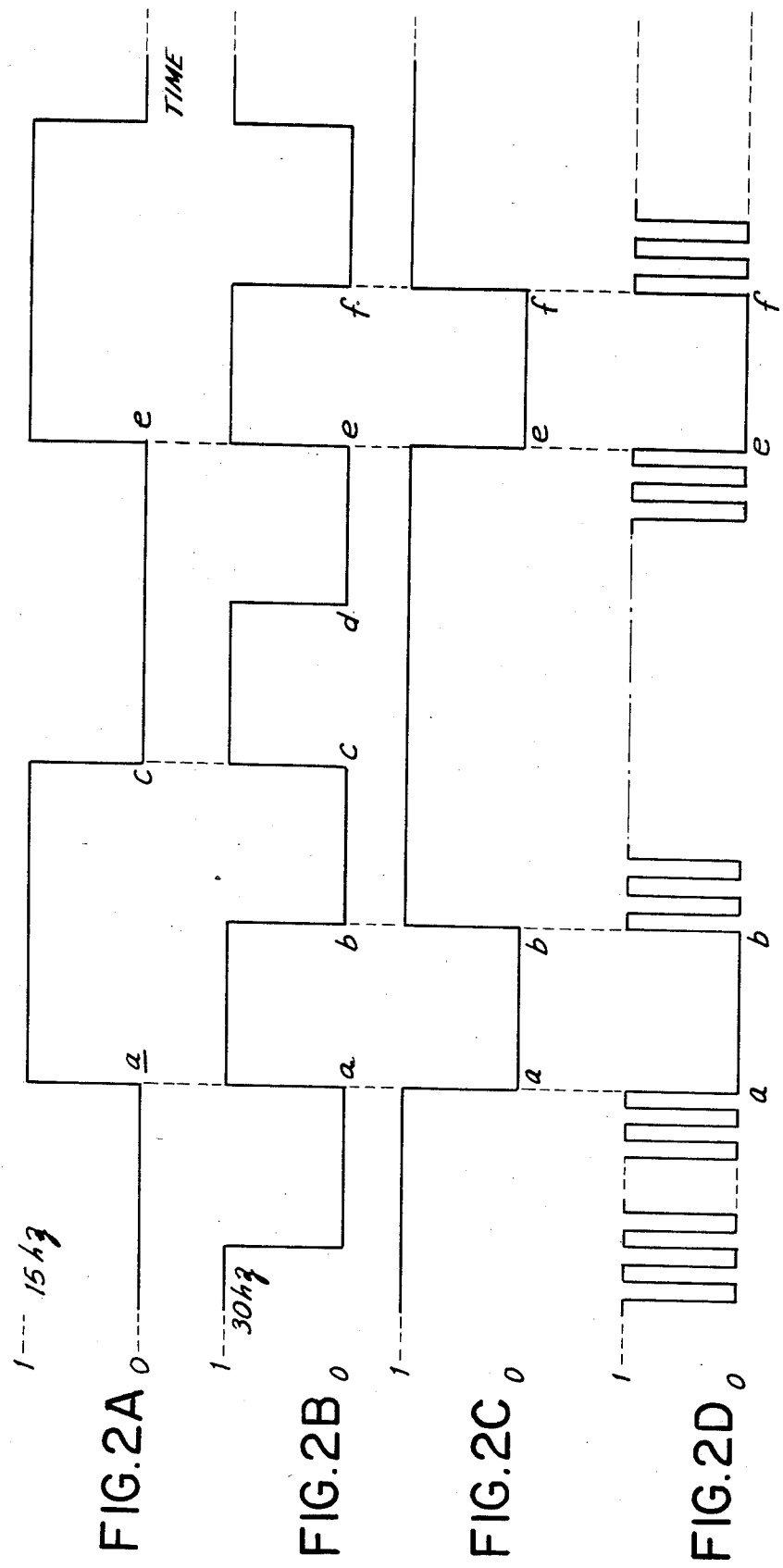

CEREBRAL PALSY TREATMENT APPARATUS AND METHODOLOGY

This application is a continuation-in-part of U.S. application Ser. No. 569,476 filed Jan. 9, 1984.

DISCLOSURE OF THE INVENTION

This invention relates to electronic pain suppression apparatus and methodology and, more specifically, to cerebral palsy treatment apparatus and procedure for treating symptoms incident to the disease.

It is an object of the present invention to provide improved cerebral palsy treatment apparatus and methodology.

More specifically, an object of the present invention is the electronic treatment of cerebral palsy in a safe, efficient and rapid manner to increase motor function and alleviate the pain and discomfort associated with the disease.

It is a further object of the present invention to provide electronic transcutaneous electronic nerve stimulating equipment operative at very low, milliampere current levels, which relieves perceived pain, and treats the symptoms of cerebral palsy.

The above and other objects and features of the instant invention are realized in a specific illustrative cerebral palsy treatment apparatus and methodology which employs a transcutaneous electronic wave to suppress perceived pain as well as all other symptoms associated with cerebral palsy. A first positive contact electrode is placed at the frontalis, and a second negative contact electrode is placed at the occiput of the head. Alternatively, the first positive contact electrode is placed at the cervical spinous process and the second negative contact electrode is placed at each affected muscle. In addition, the first positive contact may be placed at the occiput of the head and the second negative contact may be submerged in the bath tub for the patient's daily relaxation. An electronic current wave comprising relatively high frequency pulses with a low frequency modulation is then applied from the first to the second electrodes.

The above and other features and advantages of the instant invention will become more clear from the following detailed description of a specific illustrative embodiment thereof, presented hereinbelow in conjunction with the accompanying drawing, in which:

FIG. 1 is a schematic diagram of electronic cerebral palsy treatment apparatus embodying the principles of the present invention; and FIGS. 2A through 2D are wave forms illustrating the operation of the FIG. 1 apparatus.

Cerebral palsy may be defined as a disability resulting from damage to the brain before, during or after birth which is outwardly manifested by muscular incoordination and speech disturbances. Prenatal injury may be caused by a variety of factors, including diabetes, encephalocele, erythroblastosis, hydrocephalus, microcephaly, rubella, toxemia, toxoplasmosis or heredity. Postnatal injury may result from concussions, encephalitis, infection, lead poisoning, sickle cell, trauma, tumor or other causes. Most often, however, the damage which causes cerebral palsy occurs at birth; those cases are the result of anoxia, breech birth, dystocia, prematurity, respiratory distress or other causes. See O'Reilly, D. E., Walentynowic, J. E.: Etiological Factors in Cerebral Palsy: An Historical Review, *Develop Med. Child Neurol.* 1981; 23:633-642.

The apparatus of the instant invention has been found to relieve the symptoms of cerebral palsy in all subjects and to produce dramatic results with a relatively low level current and without chemical intervention.

To illustrate performance of the instant invention in overview, the apparatus of FIG. 1 is utilized to treat the symptoms associated with the diseased state of a patient who is suffering from cerebral palsy. A first positive contact electrode 60 (FIG. 1) is placed on cervical spinous process. A second negative contact electrode 72 (FIG. 1) is placed at each affected muscle. The treatments should be for 20 minutes. In addition, the first positive contact may be placed at the occiput of the head and the second negative contact may be submerged in the bath tub for the patient's daily relaxation.

An electronic wave (depicted in FIG. 2D) is applied between the first electrode 60, and the electrode 72 which are connected on common. The wave form of FIG. 2D comprises a low level (less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example characterized by a 3:1 duty cycle, being on three quarters of the time and off one quarter of the recurring period. For concreteness only and without limitation, it will hereinafter be assumed that the high frequency pulse occurs at a 15 khz rate and 1-1.5 m.a. level, while being subject to a 15 hz modulation with a 3:1 duty factor.

I have found that the wave of FIG. 2D is effective to block the pain perceived and relieve the symptoms associated with cerebral palsy. One can see a gradual increase in the patient's motor function which is accompanied by alleviation of pain.

The particular mechanism causing elimination of the symptoms of cerebral palsy is believed to follow from some increase in neural transmission to the muscles which is responsive to the low frequency modulation envelope introduced into the body, with the high frequency wave constituent serving as a transcutaneous carrier for the low frequency modulation, thereby increasing coordination and motor function.

While the precise operative mechanism may be the subject of debate, the fact of the relief of pain, reduction of spasticity, and increase in coordination is not.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass PNP transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zener diode 24 less about 7/10 of a volt for the base-emitter drop of transistor 21.

As above noted, the active power supply interval for circuit 10 of the drawing is fixed and preset to a specific period. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIGS. 2A or 2B is low (i.e., preceding the time a, during the interval b–e, —and following time f). Correspondingly, during the periods a–b and e–f when the output at divider 27 taps 29 and 30 are both high, the output of gate 33 is low (Boolean "0" value).

The wave form of FIG. 2C is supplied as one intput to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b–e, following the time f, and so forth for the recurring pattern illustrated by FIGS. 2A–2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite relief of symptoms.

In a typical application the patient is provided with the potentiometer 38. The potentiometer is first turned up so that the administered current pulses provide a noticeable tingling sensation on the patient's skin surface. The patient is then instructed to turn down the potentiometer adjustment until the sensation just disappears. This will provide the amount of transcutaneous electronic stimulation to treat the symptoms associated with the patient's disease. The potentiometer setting may be adjusted by the patient as required.

The current pulses from generator 40 pass through a protective, series limiting resistor 50 to an output terminal 51. It there flows via the lead 55 connected to terminal 51 to the electrode 60 adhered to the frontalis. The current transcutaneously passes into the patient, flows through the patient, and returns to electronic ground via the electrode pad 72 adhered to the occiput. Alternatively, electrode 60 is adhered to the cervical spinous process and electrode 72 to each affected muscle. In addition, electrode 60 may be adhered to the occiput of the head and electrode 72 may be submerged in the bathtub for a daily relaxation treatment. Electrode 72 is connected to electronic system ground via lead 70 and apparatus terminal port 52a.

As above noted, the apparatus and methodology of the instant invention treats the symptoms associated with cerebral palsy. The apparatus and methodology has manifest advantages for alleviating the patient's symptoms.

The above-described arrangement and methodology are merely illustrative of the principles of the present invention. Numerous modifications and adaptations thereof will be readily apparent to those skilled in the art without departing from the spirit and scope of the present invention.

What is claimed is:

1. A method for suppressing pain and reducing spasticity and other symptoms associated with cerebral palsy including the steps of securing a first electrode at the frontalis muscle, securing a second electrode connected electronically in common to the occiput of the subject's head, and supplying an electrical wave comprising a high frequency amplitude modulation to said first, and said second and third electrodes.

2. A method for suppressing pain and reducing spasticity and other symptoms associated with cerebral palsy including the steps of securing first electrode means at the cervical spinous process, securing second electrode means to each affected muscle, and supplying an electrical wave comprising a high frequency amplitude modulation to said first and said second electrode means.

3. The method as in claim 1 or 2, wherein the frequency of said high frequency electrical wave was in the range of 12-20 khz, wherein said low frequency modulation is in the range 8-20 hz, and wherein said wave does not exceed about 4 milliamperes.

4. The method as in claim 3, wherein said amplitude modulation is non-symmetrical.

5. A method for suppressing pain and reducing spasticity and other symptoms associated with cerebral palsy including the steps of securing a first electrode at the frontalis and securing a second electrode to the occiput of the head, and supplying an electrical wave comprising a high frequency amplitude modulation to said first and said second electrodes.

* * * * *